US010335215B2

(12) United States Patent
Biedermann et al.

(10) Patent No.: US 10,335,215 B2
(45) Date of Patent: Jul. 2, 2019

(54) BONE SCREW WITH SELF-CONSTRAINED FLEXIBILITY (71) Applicant: Biedermann Technologies GmbH & Co. KG, Donaueschingen (DE)

(72) Inventors: Lutz Biedermann, VS-Villingen (DE); Wilfried Matthis, Weisweil (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 676 days.

(21) Appl. No.: 14/511,123

(22) Filed: Oct. 9, 2014

(65) Prior Publication Data
US 2015/0105830 A1 Apr. 16, 2015

Related U.S. Application Data (60) Provisional application No. 61/889,902, filed on Oct. 11, 2013.

(30) Foreign Application Priority Data

Oct. 11, 2013 (EP) .................................. 13188243

(51) Int. Cl.
*A61B 17/86* (2006.01)
*A61B 17/70* (2006.01)
*A61B 17/68* (2006.01)

(52) U.S. Cl.
CPC ...... *A61B 17/8625* (2013.01); *A61B 17/8605* (2013.01); *A61B 17/869* (2013.01);
(Continued)

(58) Field of Classification Search
CPC .............. A61B 17/844; A61B 17/8615; A61B 17/8625; A61B 17/863; A61B 17/8635;
(Continued)

(56) References Cited

U.S. PATENT DOCUMENTS 2,524,480 A * 10/1950 Schenk ................... F16B 13/00 411/436
4,075,925 A * 2/1978 Lerich ................. F16B 13/0883 411/17
(Continued)

FOREIGN PATENT DOCUMENTS

JP 2006-501908 A 1/2006
WO WO 2012/158208 A2 11/2012

OTHER PUBLICATIONS

European Search Report; Application No. 13188243.3-1654; dated Dec. 11, 2013;5 pages.

*Primary Examiner* — Christian A Sevilla
*Assistant Examiner* — Tracy L Kamikawa
(74) *Attorney, Agent, or Firm* — Lewis Roca Rothgerber Christie LLP (57) ABSTRACT A bone screw is provided including a longitudinal core member having a longitudinal axis defining a longitudinal direction and having an outer surface and a helical groove in the outer surface, the groove being defined by opposed sidewalls; and a helical thread body configured to be accommodated in the groove. When the thread body is assembled in the groove of the core member and when the core member is straight, the thread body is configured to abut one opposed sidewall without abutting the other opposed sidewall along a full turn of the thread body, the thread body is configured to slide in the groove between the opposed sidewalls of the helical groove parallel to the longitudinal axis, and a first portion of the thread body that is outside the helical groove has a height greater than a second portion of the thread body that is in the helical groove.

22 Claims, 8 Drawing Sheets (52) U.S. Cl.
CPC ........ *A61B 17/8685* (2013.01); *A61B 17/686* (2013.01); *A61B 17/7001* (2013.01); *Y10T 29/49963* (2015.01)

(58) Field of Classification Search
CPC . A61B 17/866; A61B 17/8685; A61B 17/869; A61B 17/686; A61B 2017/8655; A61B 17/7001; F16B 35/041; F16B 37/12; F16B 37/125; F16B 5/0266; F16B 5/0275
See application file for complete search history.

(56) References Cited

U.S. PATENT DOCUMENTS

| | | | |
|---|---|---|---|
| 4,811,618 A | | 3/1989 | Takayama |
| 6,276,883 B1 | * | 8/2001 | Unsworth ............... F16B 37/12 411/16 |
| 7,935,138 B1 | | 5/2011 | Richelsoph |
| 2003/0123952 A1 | | 7/2003 | Unsworth et al. |
| 2005/0055026 A1 | | 3/2005 | Biedermann et al. |
| 2005/0154390 A1 | | 7/2005 | Biedermann et al. |
| 2008/0181746 A1 | | 7/2008 | Reiter |

* cited by examiner

BONE SCREW WITH SELF-CONSTRAINED FLEXIBILITY

CROSS-REFERENCE TO RELATED APPLICATIONS

The present disclosure claims the benefit of U.S. Provisional Patent Application Ser. No. 61/889,902, filed on Oct. 11, 2013, the contents of which are hereby incorporated by reference in their entirety, and claims priority to European Patent Application EP 13188243.3, filed on Oct. 11, 2013, the contents of which are hereby incorporated by reference in their entirety.

BACKGROUND

Field of the Invention

The invention relates to a bone screw including a longitudinal core member with a helical groove and a helical thread body that is provided in the groove. A width of the groove is greater than a width of a turn of the thread body so that the thread body is accommodated with a tolerance in the groove. This allows the thread body to slide in the groove in a longitudinal direction limited by the sidewalls of the groove. Therefore, the shank of the bone screw may move a limited amount relative to the thread body.

Description of the Related Art

A bone screw having a shank with an elastic or flexible element is known from U.S. 2005/0154390 A1. The known flexible bone screw includes a longitudinal bore and a helical, slot-shaped opening in the wall of the shank. The flexibility is determined by the geometry of the hollow bore and the helical slot-shaped opening. To limit the flexibility or to strengthen the bone screw, a core may be provided in the hollow bore.

SUMMARY

It is the object of the invention to provide a bone screw that has improved strength while simultaneously exhibiting a certain degree of flexibility and capability of dynamic motion.

The bone screw obtains its flexibility by the tolerance between the thread body and the groove provided in the surface of the screw shank.

A tension side of the bone screw is defined as the side where load is applied to the bone screw in a transverse direction, and a compression side of the bone screw is defined as the side that is compressed when the load is applied in the transverse direction. Because the thread body is configured to abut against both sidewalls of the groove, the bending load can be transferred on the compression side as well as on the tension side. Simultaneously, the bending is limited by the sidewalls of the groove acting as stop surfaces.

The micro-motion that is possible between the shank and the thread body, which is anchored in the bone, may cause a constrained motion of the bone screw, when, for example, bone resorption takes place. In such a case, the flexible motion restriction and/or control can prevent loosening of the bone anchors inside the bone.

The solid body of the core member of the bone screw facilitates bending similar to a hollow shank while simultaneously exhibiting sufficient strength. In particular, it is possible to make the shank diameter smaller compared to shanks having a hollow bore.

When the core member and the thread body have a different pitch, it is possible to bias the thread body against the core member.

Because the thread body is a separate part that is attachable to the core member, the bone screw is a modular device that allows one to select a suitable thread body in terms of thread pitch and/or thread form and to mount it to a core member. In such a configuration, the thread body is able to maintain compression or distraction relative to the core member in the longitudinal direction.

BRIEF DESCRIPTION OF THE DRAWINGS

Further features and advantages will become apparent from the description of embodiments by means of the accompanying drawings. In the drawings:

FIG. 4a shows a cross-sectional view of the bone screw along the line A-A in FIG. 3.

FIG. 4b shows an enlarged cross-sectional view of a detail of FIG. 4a.

FIG. 5a shows a cross-sectional view of the bone screw shown in FIG. 3 in a state in which load is applied to the bone screw in a transverse direction.

FIG. 5b shows an enlarged cross-sectional view of a detail of FIG. 5a.

FIG. 17a shows a cross-sectional view of the bone screw shown in FIG. 16, the cross-section taken in a plane containing the screw axis.

FIG. 17b shows an enlarged cross-sectional view of a detail shown in FIG. 17a.

FIG. 19b shows an enlarged view of a portion of the bone screw during the insertion step shown in FIG. 19a.

FIG. 20b shows an enlarged view of a portion of the bone screw in the state shown in FIG. 20a.

DETAILED DESCRIPTION

Figures 1, 2:
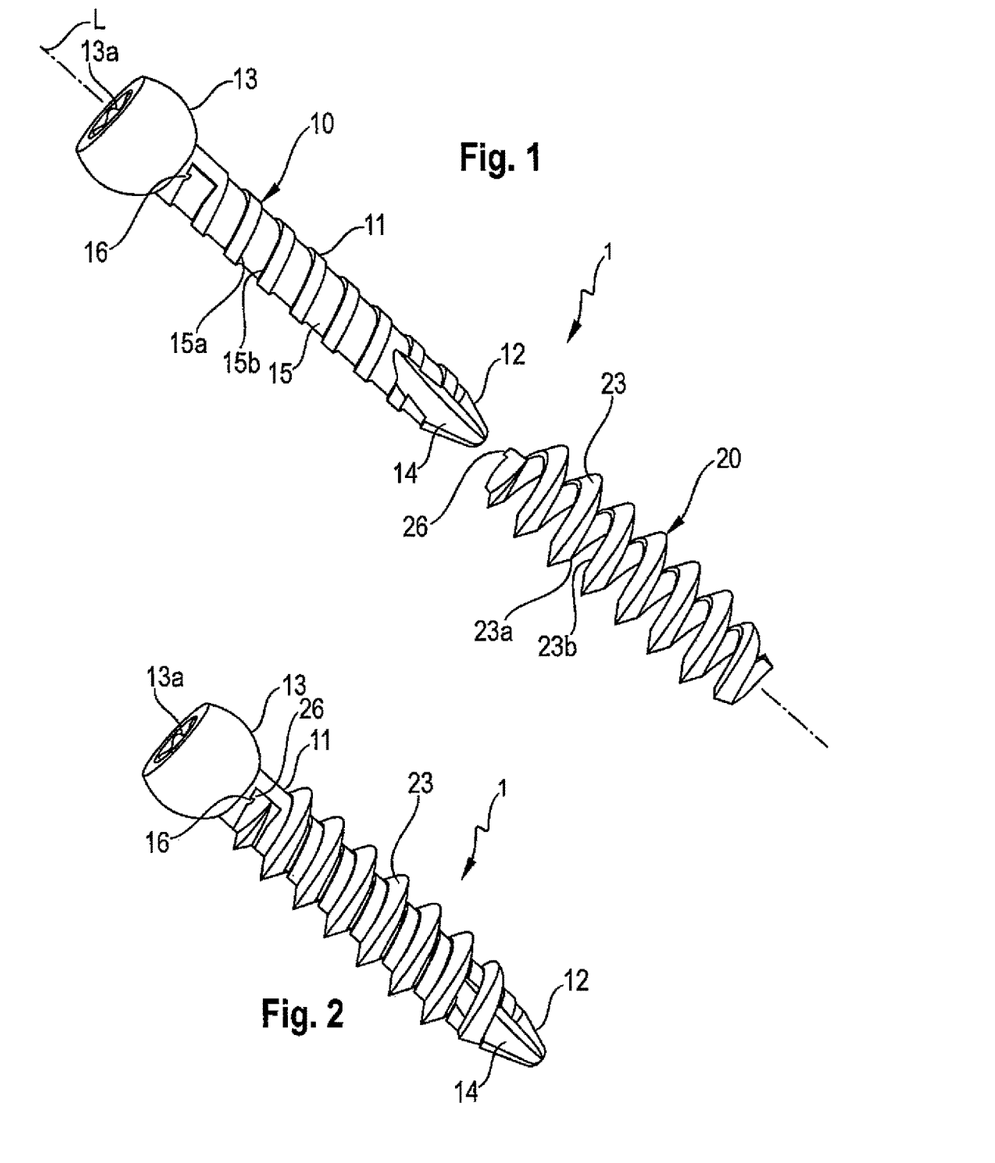
FIG. 1 shows a perspective exploded view of a bone screw according to a first embodiment.
FIG. 2 shows a perspective view of the bone screw of FIG. 1.

FIGS. 1 and 2 depict a first embodiment of a bone screw 1 that is established as a two-piece unit including a core member 10 and a thread body 20 as a separate part. The thread body 20 is mounted to the core member 10 and the two pieces are movable relative to one another to a pre-defined extent. Referring in more detail to FIGS. 3 to 7, the core member 10 includes a shank 11 with a tip 12 at one end of the shank 11 and a head 13 at an opposite end of the shank 11. The shank 11 defines the screw axis or longitudinal axis L. The head 13 may be equipped with a recess 13a provided at its free end surface for engagement with a tool. The shape of the head 13 is shown to be spherical segment-shaped but is not limited thereto. Any shape of the head may be contemplated. At least one but preferably a plurality of notches 14 may be provided in the shank 11 that extend in a longitudinal direction from a position on the shank 11 to the tip 12. The notches 14 may be slightly twisted with respect to the longitudinal axis. They may serve for allowing self-cutting of a bone by the bone screw during insertion. At the tip 12, the shank 11 tapers towards the free end.

Figure 6:
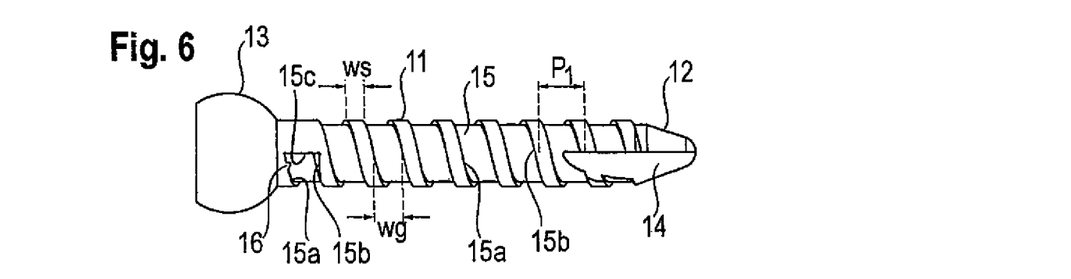
FIG. 6 shows a side view of the core member of the bone screw of FIG. 1.

In the outer surface of the shank 11, a helical groove 15 is provided that extends from a position close to the head 13 to a position at the beginning of the tapered section of the tip 12. The helical groove 15 has a width wg in the longitudinal direction that may be greater than a width ws of the shank portions that lie between two turns of the helical groove 15. As can be seen in particular in FIGS. 4a to 5b, a cross-section of the groove 15 is substantially rectangular. A depth d of the groove is less than the width wg of the groove. Opposing sidewalls 15a, 15b of the groove form abutment surfaces (e.g., stop surfaces) for the thread body 20 as further described below. A first sidewall 15a is facing the tip 12 and a second sidewall 15b is facing the head 13. An end portion of the groove 15 that is close to the head 13 has an end surface 15c (e.g., a transverse wall) extending substantially in the longitudinal direction. In a side view, as seen in FIG. 6, the end portion of the groove has a substantially trapezoidal contour, i.e., the sidewalls 15a, 15b are slightly angled with respect to each other in such a manner that the groove 15 widens towards the transverse wall 15c. As can be seen in particular in FIGS. 1 and 6, a nose-shaped projection 16 extends from the first sidewall 15a into the end portion of the groove 15. The nose-shaped projection 16 is formed such that it cooperates with a corresponding portion of the thread body in order to retain the thread body in the groove 15.

The number of turns of the groove 15 corresponds to the number of thread turns of a bone screw thread typically provided on a bone screw. The orientation of the helical groove corresponds to that of a right-hand thread. A thread pitch of the helical groove 15 forms a first thread pitch $P_1$ of the bone screw 1.

Figure 3:
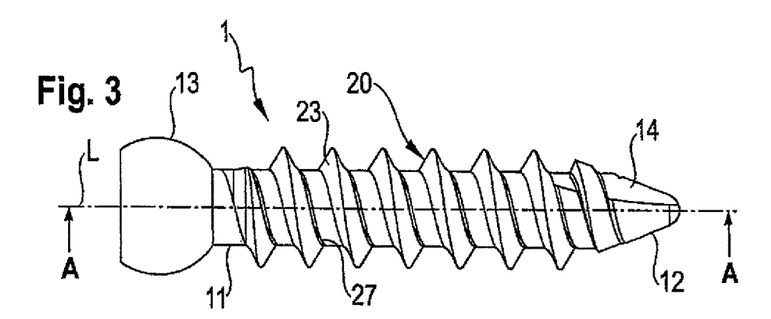
FIG. 3 shows a side view of the bone screw of FIG. 2.

An end portion of the groove 15 that is opposite to the head 13 is open towards the tip 12 and ends substantially at a position where the shank tapers to form the tip 12 (see, for example, FIGS. 3 and 6). The open end portion of the groove 15 allows the groove 15 to engage with the thread body 20 from the tip end of the shank 11.

The core member 10 is a monolithic, solid piece without a coaxial bore. Because of this, the shank diameter can be reduced compared to screw shanks that have a hollow, coaxial bore.

Figures 4A, 4B, 5A, 5B:
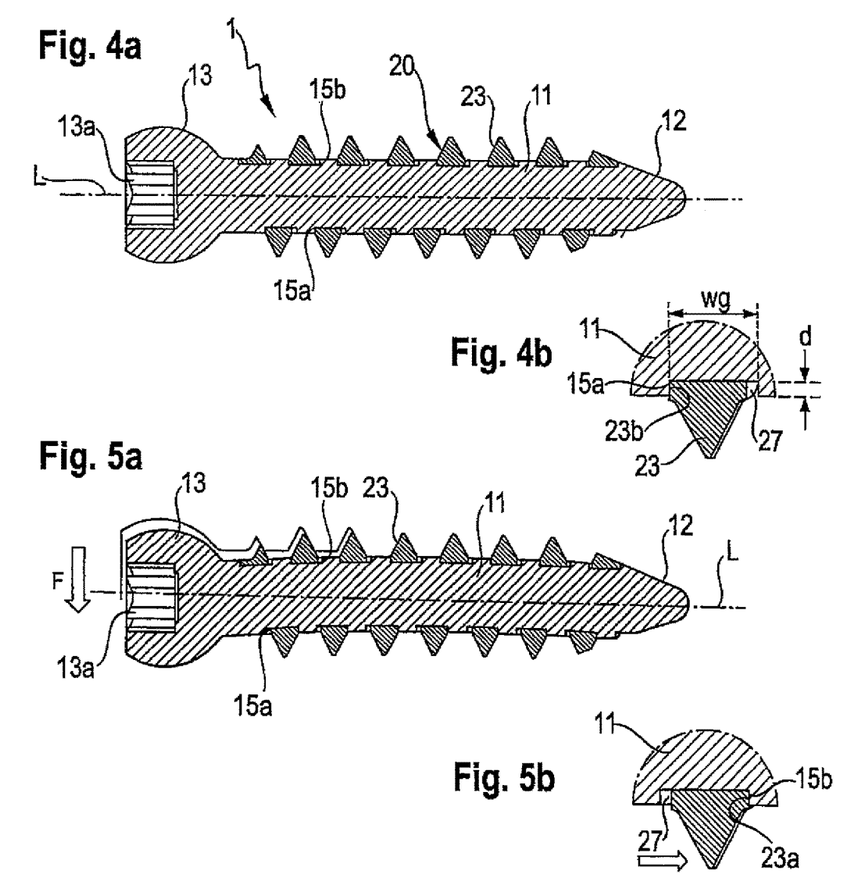
Figure 7:
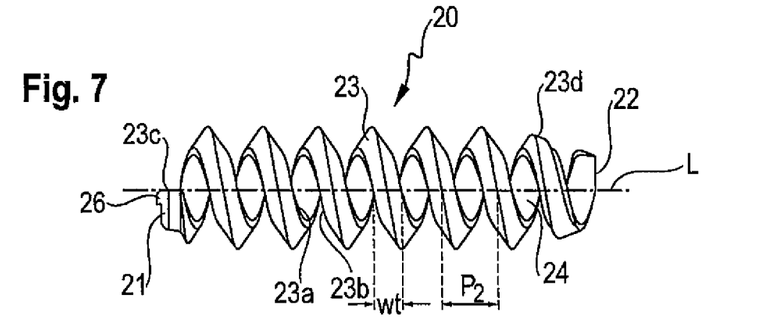
FIG. 7 shows a side view of the thread body of the bone screw shown in FIG. 1.

As depicted in particular in FIGS. 1 and 7, the thread body 20 is a substantially hollow, cylindrical member with a first end 21 and an opposite second end 22 and includes a helical thread 23, the turns of which wind around a hollow interior section 24. The thread 23 has the shape of a usual bone thread having a substantially triangular cross-section with a base including opposing surfaces 23a, 23b that extend substantially perpendicular to the longitudinal axis in a cross-sectional view as seen in FIG. 4a and FIG. 4b. A height of the opposing surfaces 23a, 23b is the same or substantially greater than a depth of the groove 15 as depicted in FIG. 4b. The opposing surfaces 23a, 23b of the base of the thread 23 are configured to cooperate with the opposing sidewalls 15a, 15b of the groove 15.

A width wt of a thread turn of the thread body 20 is less than the width wg of the groove 15, so that the thread body 20 can be placed into the groove 15 with a tolerance. The thread pitch of the thread body 20 is a second thread pitch $P_2$. In this embodiment, the second thread pitch $P_2$ is the same as the first thread pitch $P_1$ of the helical groove 15. An end surface 23c of the thread body 20 at the first end 21 extends substantially coaxially to the longitudinal axis L and is configured to abut against the end surface 15c of the groove 15. The thread-direction of the thread 23 is the same as that of the groove 15 so that the thread body 20 can be screwed onto the shank 11, thereby engaging the groove 15. Close to the end surface 23c, there is a nose-shaped projection 26 of the thread body 20 that is configured to cooperate with the nose-shaped projection 16 at the end portion of the groove 15 such that, when the nose-shaped projection 26 engages the nose-shaped projection 16, the thread body 20 is retained in the groove 15 and the core member 10 is prevented from being screwed out of the thread body 20.

At the second end 22, the height of the crest of the thread 23 decreases continuously while an inclination of the flank that faces towards the second end 22 continuously decreases. As can be seen in FIGS. 2 and 5a, the last turn of the thread 23 of the thread body 20 or a portion thereof has a smaller outer diameter than the remainder of the thread body 20 to match the shape of the tip 12.

The bone screw 1 is assembled by screwing the thread body 20 from the tip end of the shank onto the shank 11. Thereby, the first end 21 of the thread body 20 engages the groove 15 and the thread body 20 is advanced until its first end 21 reaches the end portion of the groove 15. The nose-shaped projection 26 of the thread body slides along the nose-shaped projection 16 that projects into the groove until it snaps behind it and the projections engage each other. When the nose-shaped projection 26 passes along the nose-shaped projection 16, the enlarged end portion of the groove 15 provides the necessary space to accommodate the first end 21. In the mounted state, the end surface 23c of the thread body 20 abuts against the end surface 15c of the groove 15 of the shank 11. When the thread body 20 is fully mounted onto the shank, the sidewall 23b of the thread body 20 that is facing the head 13 abuts against the sidewall 15a of the groove 15 as can be seen in FIGS. 3 to 4b. Because the width wg of the groove 15 is larger than the width wt of the thread 23, there is a gap 27 between the sidewall 23a of the thread body 20 and the second sidewall 15b of the groove that allows the thread body to move in a longitudinal direction relative to the shank 11 until the sidewall 23a of the thread body 20 abuts against the sidewall 15b of the groove 15.

The core member 10 and the thread body 20 are both made of a body-compatible material. Such body-compatible materials are, in particular, body-compatible metals, such as titanium and stainless steel, or body-compatible metal alloys, such as nickel-titanium (NiTi) alloys, for example, Nitinol. Body-compatible plastics are, for example, PEEK (polyetheretherketone). The core member 10 and the thread body 20 can be made of the same or of different materials. For example, the core member 10 can be made of a body-compatible metal or metal alloy and the thread body 20 can be made of a body-compatible plastic material. Any other combination of materials may also be contemplated.

The use of the dynamic bone screw will be explained by referring to FIGS. 4a to 5b. When the bone screw 1 is inserted into a core hole prepared in a bone, a bone part, or a vertebra, for example, a pedicle of a vertebra, the core member 10 is in a straight state. Because the nose-shaped projections 26, 16 of the thread body 20 and the groove 15, respectively, are engaged with each other, the turning motion of the bone screw when it is inserted does not cause the thread body 20 to disengage from the groove 15. Further, the turning motion has the effect that the thread body 20 abuts with its sidewall 23b against the first sidewall 15a of the groove 15 that faces the tip 12.

When load is applied to the bone screw in a direction transverse to the longitudinal direction and a transverse force F acts on the core member 10, for example, on the head 13, the side of the bone screw 1 to which the load is applied is defined as the tension side of the bone screw and the opposite side is defined as the compression side of the bone screw 1. The core member bends with respect to the longitudinal axis L while the thread body 20 still engages the surrounding bone material. Hence, the bending of the core member 10 relative to the thread body 20 causes the thread turns of the thread body 20 to move towards the opposite sidewall 15b of the groove 15 on the compression side as can be seen in FIGS. 5a and 5b. Simultaneously, on the tension side, the side surface 23b of the thread turns of the thread body 20 still abut against the first sidewall 15a of the groove 15. Therefore, the sidewalls 15a, 15b of the groove provide stops for motion of the core member 10 relative to the thread body 20. This permits limited micro-motion between the shank 11 and the thread body 20 that is anchored in surrounding bone material. In addition, the load can be transferred not only on the compression side, but also on the tension side when the sidewall 23b abuts against the sidewall 15a of the groove 15.

The bone screw may be used, for example, as a pedicle screw. In this case, it can be connected to a receiving part to form a polyaxial or a mono-planar bone anchor. For the receiving part, all kinds of receiving parts can be used that pivotably hold the head of the bone screw and connect the bone screw to a spinal stabilization rod. When the vertebrae move, transverse forces may act on the pedicle screw. Due to the limited flexibility, the core member of the pedicle screw can bend and, thus, prevent a fracture of weak bone material. Also, in the case of bone resorption, the bone screw 1 may balance forces due to its dynamic characteristics that would otherwise have an adverse effect on the stabilization device. In particular, loosening of the bone screw 1 in the bone due to bone resorption can be prevented.

Figure 8A:
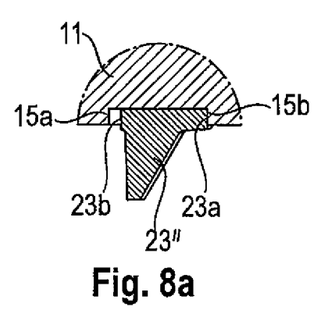
FIGS. 8a-8d show enlarged cross-sectional views of a portion of FIG. 4a with various modifications of the shape of the thread body.
Figure 8B:
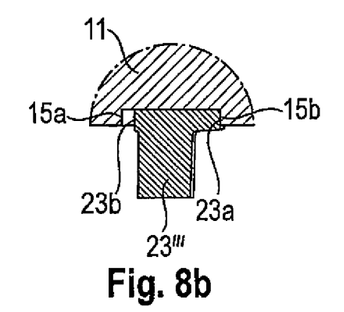
Figure 8C:
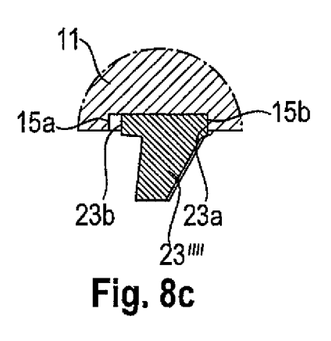
Figure 8D:
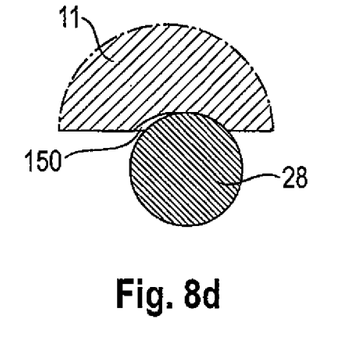
Figure 9:
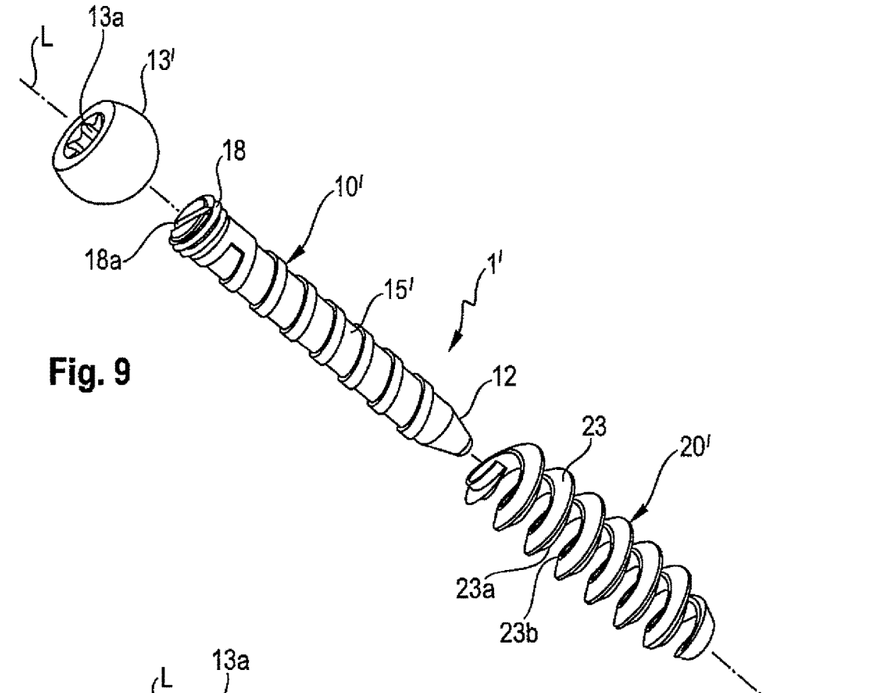
FIG. 9 shows an exploded perspective view of a second embodiment of a bone screw.

Because the core member 10 and the thread body 20 are separate parts, a modular bone screw can be provided, wherein different combinations of core member 10 and thread body 20 may be selected. For example, the thread body 20 can be designed to have various thread forms, and a particular thread body 20 with a specific thread form can be mounted to the core member 10. FIGS. 8a to 8d depict various thread forms that may be used. FIG. 8a shows a thread 23" with a saw-tooth shape that includes a horizontal flank facing the head 13 and an opposite inclined flank. FIG. 8b shows a thread 23''' that has a substantially square shape including two opposite horizontal flanks. FIG. 8c shows a thread 23'''' including a flank that faces the head 13 which has a negative thread angle. FIG. 8d shows a further modification of the design of the groove and the thread body. The groove 150 is a helix-shaped groove with a circular segment-shaped cross-section, and the thread body includes a thread helix 28 made of a round wire.

Figure 10:
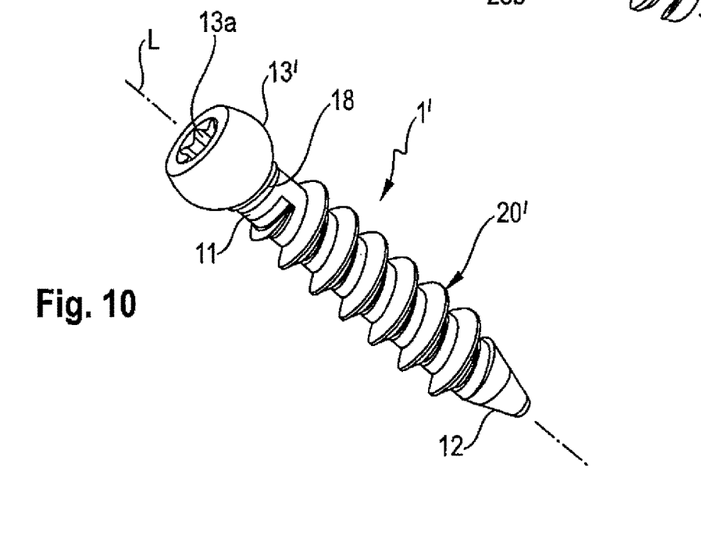
FIG. 10 shows a perspective view of the assembled bone screw according to the second embodiment.
Figure 11:
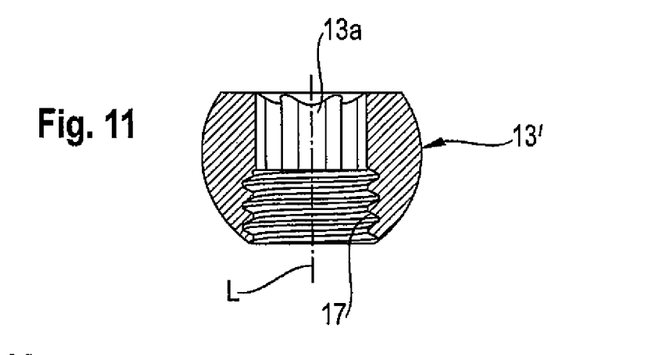
FIG. 11 shows a cross-sectional view of the head of the bone screw according to the second embodiment, the cross-section taken in a plane containing the screw axis.
Figure 12:
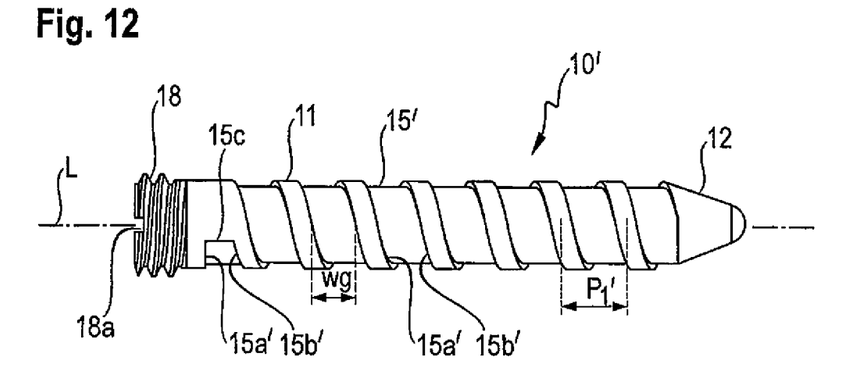
FIG. 12 shows a side view of the core member of the bone screw according to FIG. 9.
Figure 13:
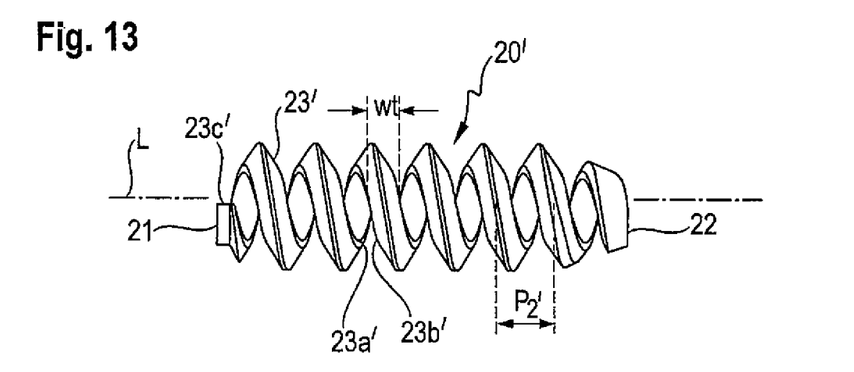
FIG. 13 shows a side view of the thread body of the bone screw according to FIG. 9.
Figure 14:
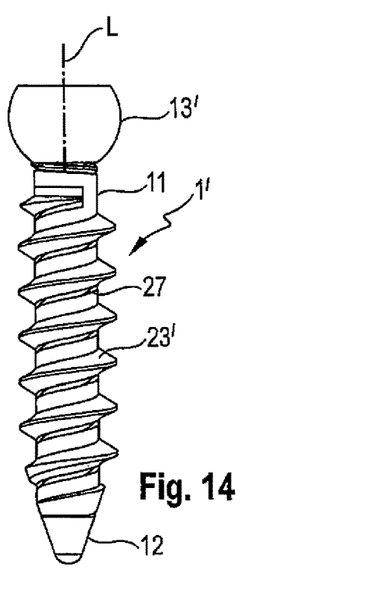
FIG. 14 shows a side view of the bone screw according to the second embodiment in a first state.
Figure 15:
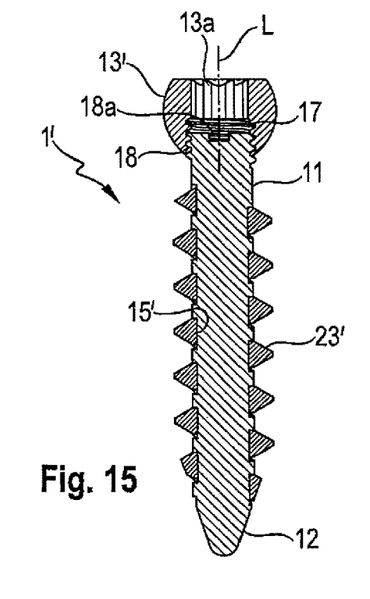
FIG. 15 shows a cross-sectional view of the bone screw shown in FIG. 14, the cross-section taken in a plane containing the screw axis.

A second embodiment of the bone screw will be described with reference to FIGS. 9 to 16. Parts and portions that are identical or similar to that of the first embodiment are marked with the same reference numerals, and the description thereof will not be repeated. The bone screw 1' includes a core member 10', a separate head 13', and a thread body 20'. Referring in particular to FIGS. 11 to 13, the core member 10' includes the shank 11 with the tip 12 at one end and a threaded portion 18 at the end opposite to the tip 12 that has an outer thread for connection to the separate head 13'. At the free end-surface of the threaded portion 18, a slit 18a or another engagement portion for a screwdriver is provided. The head 13' includes a threaded bore 17 at its side opposite to the engagement recess 13a that is in communication with the engagement recess 13a. An axial length of the threaded bore 17 is greater than an axial length of the threaded portion 18 of the shank 11 so that a total length in the longitudinal direction of the bone screw 1' can be varied by screwing the shank 11 more or less into the threaded bore 17.

The groove 15' differs from the groove 15 of the first embodiment in particular due to an end section thereof that is close to the threaded portion 18. In particular, the first sidewall 15a' that faces away from the threaded portion 18 extends at an angle substantially 90° to the longitudinal axis L. There is also no nose-shaped projection. The opposing second sidewall 15b' at the end section has the same inclination throughout the shank 11. The pitch of the groove 15' is a first pitch $P_1'$.

The thread body 20' differs from the thread body 20 of the first embodiment mainly due to its shape at the first end 21. The shape at the first end 21 corresponds to the shape of the groove 15'. Consequently, it does not have a nose-shaped projection, either. As can be seen in FIG. 10, the first end 21 of the thread body 20' fits into the end section of the groove 15' with a tolerance.

The pitch of the thread 23' of the thread body 20' is a second pitch $P_2'$. In this embodiment, the second pitch $P_2'$ is different from the first pitch $P_1'$ of the groove 15'. The second pitch $P_2'$ can be greater or less than the first pitch $P_1'$. In the specific embodiment shown, the second pitch $P_2'$ is less than the first pitch $P_1'$.

The bone screw 1' is assembled by screwing the thread body 20' onto the shank 11 of the core member 10' until the first end 21 of the thread body 20' is accommodated in the end section of the groove 15'. Because the first pitch $P_1'$ is different from the second pitch $P_2'$, the thread body 20' is biased against the core member 10'. In the embodiment, the thread body 20' is slightly extended in order to fit into the groove 15' having the greater pitch. The head 13' is mounted to the threaded portion 18 of the shank 11.

Figure 16:
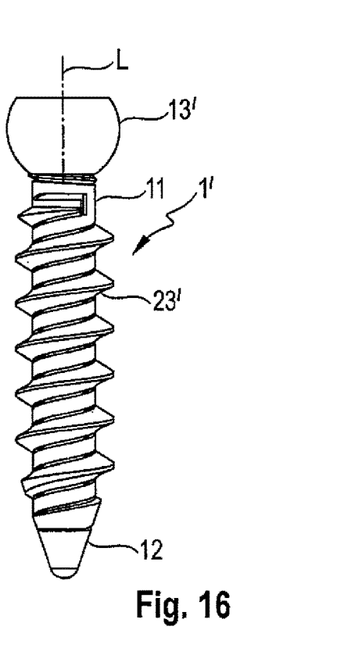
FIG. 16 shows a side view of the bone screw according to the second embodiment in a second state.
Figures 17A, 17B:
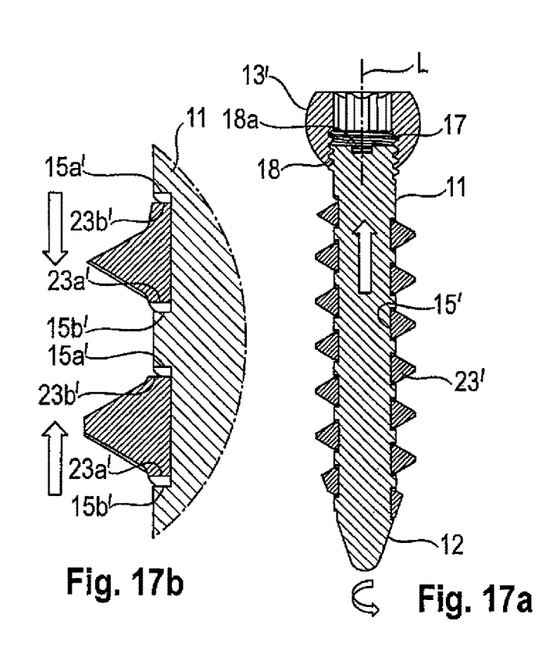

The function of the bone screw 1' will be described referring to FIGS. 15 to 17*b*. When the thread body 20' is mounted onto the shank 11, a second surface 23*b*' of the thread 23' abuts against the first sidewall 15*a*' of the groove that faces away from the head 13'. Next, as shown in FIGS. 16 to 17*b*, the shank 11 is turned with a tool engaging the engagement slit 18*a* to move the shank slightly into the head 13' while the thread body 20' remains engaged with the bone. In this condition, the threads move away from the first sidewall 15*a*' of the groove and move towards the middle of the groove, as shown in FIGS. 17*a* and 17*b*. Due to the different pitch, the biased thread body 20' exerts a compressing force onto the bone that is between the thread turns of the thread 23', as depicted in FIG. 17*b*. This prevents loosening of the bone screw in the bone. In a similar manner, when the second pitch $P_2'$ associated with the thread body 20' is greater than the first pitch $P_1'$ associated with the groove 15', the thread body 20' has to be compressed in order to fit into the groove 15'. As a result thereof, it exerts a distraction force (e.g., an expansion force) onto the surrounding bone in a longitudinal direction.

Figure 18:
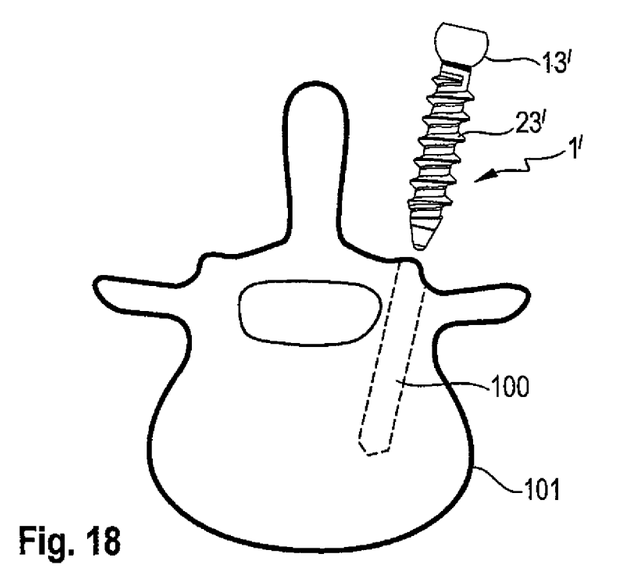
FIG. 18 shows a schematic view of a first step of inserting the bone screw according to the second embodiment into a pedicle of a vertebra.
Figure 19A:
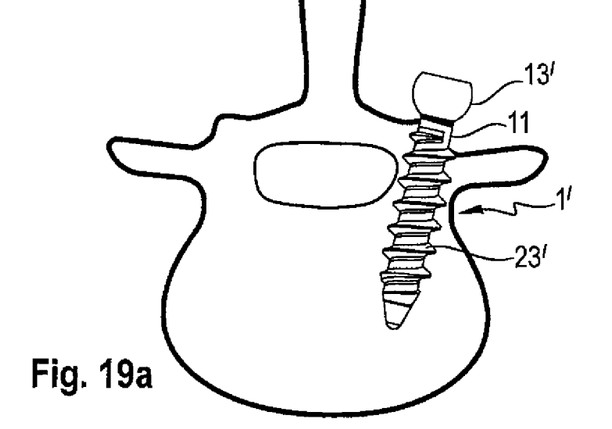
FIG. 19a shows a schematic view of a second step of inserting the bone screw according to the second embodiment into the pedicle of a vertebra.
Figure 19B:
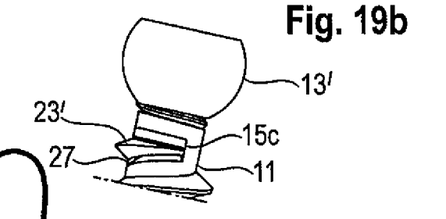
Figure 20A:
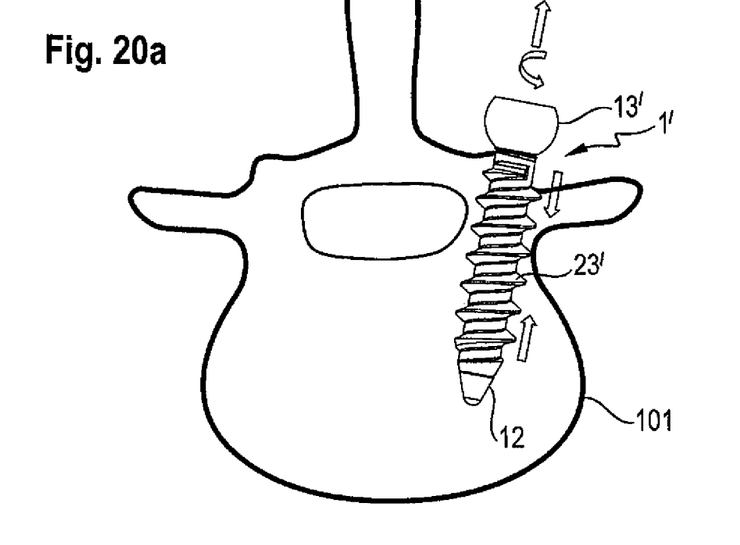
FIG. 20a shows a third step of the insertion procedure of the bone screw according to the second embodiment.
Figure 20B:
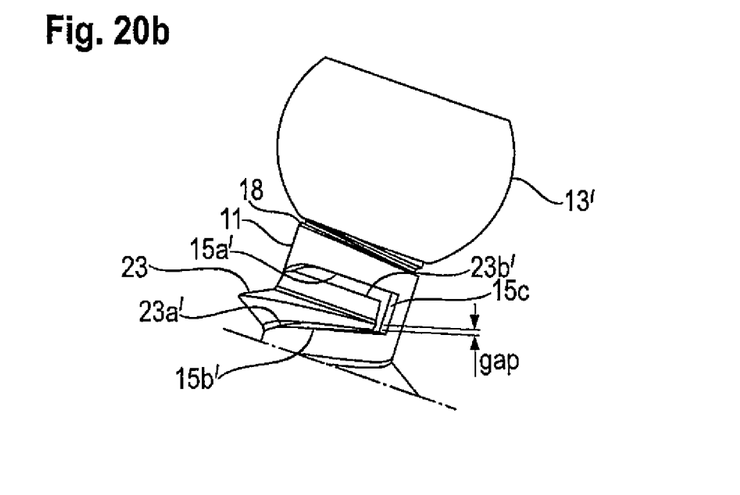

The clinical application will be described with reference to FIGS. 18 to 20*d*. First, as shown in FIG. 18, the assembled bone screw 1' is inserted into a prepared core hole 100 in the pedicle of a vertebra 101. When it is fully inserted, the thread body 20' abuts against the first sidewall 15*a*' of the groove 15', as shown in FIGS. 19*a* and 19*b*. In this condition, the thread body 20' is biased against the core member 10'. In a next step, as shown in FIGS. 20*a* and 20*b*, the shank 11 is moved deeper into the head 13'. Because the thread body 20' is anchored in the bone, the thread 23' is separated from the abutment provided by the first sidewall 15*a*' of the groove 15' in an axial direction, thereby creating a gap on both sides of the thread in the groove (FIG. 20*b*). The biasing force of the thread body 20' in relation to the shank 11 exerts a compression force onto the bone.

In addition, a bending of the core member 10' away from the longitudinal axis is possible as described in connection with the first embodiment.

The bone screw 1' according to the second embodiment is also a modular bone screw. The core member 10' and the thread body 20' may be manufactured of the same or of different materials like the bone screw according to the first embodiment. Also, various thread forms can be selected for the thread body 20'.

Various other modifications of the embodiment may be contemplated. The groove may extend only along a portion of the shank, and the thread body may cover only the portion of the shank where the groove is provided.

In a further modified embodiment, the width of the groove can vary along the length of the groove. For example, the relation wg/wt of the width of the groove wg to the width of the thread body wt can be such that it increases from 1 at the tip to a value greater than 1 towards the head. In this case, the thread body is accommodated in the groove without a tolerance at the tip side and with a tolerance at the head side.

The head may have different shapes, such as a lens-shape, a disc-shape, or any other shape. The bone screw according to the first and also according to the second embodiment may even be provided without a head. The bone screw may also be used together with a bone plate. The tip may have a different shape or may even be omitted.

In a further embodiment, the head is spherical segment-shaped as shown in FIG. 1, for example, and is pivotally accommodated in a receiving part so that a polyaxial or a monoplanar bone screw is formed that can be connected to a rod. Instead of the spherical segment-shaped head, a receiving part for a rod may be provided at the end of the shank to form a monoaxial bone screw that can be connected to a rod.

What is claimed is:

1. A bone screw comprising:
   a longitudinal core member defining a longitudinal axis and having an outer surface and a helical groove recessed from the outer surface, the helical groove having a groove cross-section defined by opposed sidewalk and a bottom surface connecting the opposed sidewalk and forming a first portion of the groove cross-section that is positioned closest radially to the longitudinal axis, wherein a minor diameter of the core member measured radially between diametrically opposite portions of the bottom surface of the helical groove is greater than a depth of the helical groove measured radially from the first portion of the groove cross-section to the outer surface of the core member; and
   a helical thread body configured to be accommodated in the helical groove,
   wherein when the thread body is assembled in the helical groove of the core member and when the core member is straight along the longitudinal axis, the thread body is configured to abut one opposed sidewall without abutting the other opposed sidewall along a full turn of the thread body,
   wherein when the thread body and the core member are assembled and the thread body is contacting the bottom surface of the helical groove, a portion of the thread body that extends outside the helical groove has a height measured radially outwardly from the outer surface of the core member that is greater than the depth of the helical groove over an uninterrupted length of the thread body that covers a majority of the entire thread body, and
   wherein the thread body is configured to slide in the helical groove between the opposed sidewalls of the helical groove in a direction parallel to the longitudinal axis.

2. The bone screw of claim 1, wherein the longitudinal core member is a solid body.

3. The bone screw of claim 1, wherein the helical groove has a first end and a second end, and comprises a first engagement portion at the second end, and wherein the thread body comprises a second engagement portion that is configured to engage the first engagement portion to hold the thread body in the helical groove.

4. The bone screw of claim 3, wherein the first end of the helical groove is open.

5. The bone screw of claim 3, wherein the core member has a first end and a second end and comprises a head at the second end of the core member, and wherein the first and second engagement portions are adjacent the head.

6. The bone screw of claim 1, wherein the opposed sidewalls of the helical groove comprise a first sidewall and an opposite second sidewall as a first stop and a second stop, respectively, and the first and second sidewalls are parallel to limit the sliding of the thread body along the longitudinal axis.

7. The bone screw of claim 6, wherein the thread body is configured to abut the first sidewall when no transverse load is applied to the core member.

8. The bone screw of claim 6, wherein, when a transverse load is applied to the core member, the thread body is configured to slide in the helical groove in the direction parallel to the longitudinal axis until portions of the thread body abut the second sidewall.

9. The bone screw of claim 1, wherein the helical groove has a first pitch and the thread body has a second pitch, and wherein the first pitch and the second pitch are the same as each other.

10. The bone screw of claim 1, wherein the helical groove has a first pitch and the thread body has a second pitch, and wherein the first pitch and the second pitch are different from each other.

11. The bone screw of claim 1, wherein the core member has a first end and a second end, and comprises a tip portion at the first end, and wherein an end of the thread body has a smaller outer diameter than adjacent portions of the thread body, and the smaller outer diameter matches an outer diameter of the tip portion.

12. The bone screw of claim 1, wherein the core member has a first end and a second end, and comprises a head at the second end.

13. The bone screw of claim 12, wherein the core member further comprises a shank, wherein the head and the shank are separable, and wherein the head is configured to be connected to the shank.

14. The bone screw of claim 13, wherein the shank comprises a threaded portion having an outer thread, and wherein the head has a threaded bore that is configured to engage the threaded portion of the shank.

15. The bone screw of claim 1, wherein the thread body has a flat inner surface configured to extend parallel to the longitudinal axis when the thread body is assembled in the helical groove of the core member, the flat inner surface having a width measured in the direction parallel to the longitudinal axis that is greater than half of a width of the helical groove measured in the direction parallel to the longitudinal axis.

16. The bone screw of claim 1, wherein when the thread body is assembled in the helical groove of the core member, the thread body has a first surface configured to abut the one opposed sidewall of the helical groove, such that in a cross-sectional plane including the longitudinal axis, the first surface is flat and configured to extend parallel to the one opposed sidewall.

17. A bone screw comprisng:
a longitudinal core member defining a longitudinal axis and comprising a helical projection with an outer surface, the helical projection defining a helical groove extending between adjacent turns of the helical projection, the helical groove having a groove cross-section defined by opposed sidewalk of adjacent turns of the helical projection and a bottom surface connecting the opposed sidewalk and forming a first portion of the groove cross-section that is positioned closest radially to the longitudinal axis, wherein a width of the helical groove measured in a direction parallel to the longitudinal axis is greater than a depth of the helical groove measured radially from the first portion of the groove cross-section to the outer surface of the helical projection; and
a helical thread body configured to be accommodated in the helical groove,
wherein when the thread body is assembled in the helical groove of the core member and when the core member is straight along the longitudinal axis, the thread body is configured to abut one opposed sidewall without abutting the other opposed sidewall along a full turn of the thread body and is slidable along the longitudinal axis to abut the other opposed sidewall,
wherein when the thread body and the core member are assembled and the thread body is contacting the bottom surface of the helical groove, a portion of the thread body that extends outwardly past the helical projection has a height measured radially outwardly from the outer surface of the helical projection that is greater than the depth of the helical groove over an uninterrupted length of the thread body that covers a majority of the entire thread body, and
wherein the thread body is configured to slide in the helical groove between the opposed sidewalls of the helical groove in the direction parallel to the longitudinal axis.

18. A method of assembling a bone screw, the method comprising:
selecting a longitudinal core member defining a longitudinal axis and having an outer surface and a helical groove recessed from the outer surface, the helical groove having a groove cross-section defined by opposed sidewalls and a bottom surface connecting the opposed sidewalls and forming a first portion of the groove cross-section that is positioned closest radially to the longitudinal axis, wherein a minor diameter of the core member measured radially between diametrically opposite portions of the bottom surface of the helical groove is greater than a depth of the helical groove measured radially from the first portion of the groove cross-section to the outer surface of the core member;
selecting a helical thread body configured to be accommodated in the helical groove; and
screwing the helical thread body onto the helical groove of the core member,
wherein when the thread body is assembled in the helical groove of the core member and when the core member is straight along the longitudinal axis, the thread body is configured to abut one opposed sidewall without abutting the other opposed sidewall along a full turn of the thread body,
wherein when the thread body and the core member are assembled and the thread body is contacting the bottom surface of the helical groove, a portion of the thread body that extends outside the helical groove has a height measured radially outwardly from the outer surface of the core member that is greater than the depth of the helical groove over an uninterrupted length of the thread body that covers a majority of the entire thread body, and
wherein the thread body is configured to slide in the helical groove between the opposed sidewalls of the helical groove in a direction parallel to the longitudinal axis.

19. The method of claim 18, wherein the helical groove has a first pitch and the thread body has a second pitch, and wherein the first pitch and the second pitch are the same as each other.

20. The method of claim 18, wherein the helical groove has a first pitch and the thread body has a second pitch, and wherein the first pitch and the second pitch are different from each other.

21. A method of inserting a bone screw into a bone, the bone screw comprising a longitudinal core member defining a longitudinal axis and having an outer surface and a helical groove recessed from the outer surface, the helical groove having a groove cross-section defined by opposed sidewalls and a bottom surface connecting the opposed sidewalks and forming a first portion of the groove cross-section that is positioned closest radially to the longitudinal axis, wherein a minor diameter of the core member measured radially between diametrically opposite portions of the bottom surface of the helical groove is greater than a depth of the helical groove measured radially from the first portion of the groove cross-section to the outer surface of the core member, and a helical thread body configured to be accommodated in the helical groove, wherein when the thread body is assembled in the helical groove of the core member and when the core member is straight along the longitudinal axis, the thread body is configured to abut one opposed sidewall without abutting the other opposed sidewall along a full turn of the thread body, wherein when the thread body and the core member are assembled and the thread body is contacting the bottom surface of the helical groove, a portion of the thread body that extends outside the helical groove has a height measured radially outwardly from the outer surface of the core member that is greater than the depth of the helical groove over an uninterrupted length of the thread body that covers a majority of the entire thread body, and wherein the thread body is configured to slide in the helical groove between the opposed sidewalls of the helical groove in a direction parallel to a longitudinal axis, the method comprising:

preparing a core hole in the bone;

assembling the helical thread body onto the helical groove of the core member; and     inserting the longitudinal core member with the thread body into the core hole.

22. The method of claim 21, further comprising:

attaching a head onto the core member before inserting the longitudinal core member into the core hole; and     after inserting the longitudinal core member into the core hole, retracting the core member into the head.

\* \* \* \* \*

UNITED STATES PATENT AND TRADEMARK OFFICE
CERTIFICATE OF CORRECTION

PATENT NO. : 10,335,215 B2  
APPLICATION NO. : 14/511123  
DATED : July 2, 2019  
INVENTOR(S) : Lutz Biedermann et al.

Page 1 of 1

It is certified that error appears in the above-identified patent and that said Letters Patent is hereby corrected as shown below:

In the Claims

| | |
|---|---|
| Column 8, Line 11, Claim 1 | delete "sidewalk" and insert -- sidewalls -- |
| Column 8, Line 12, Claim 1 | delete "sidewalk" and insert -- sidewalls -- |
| Column 9, Line 43, Claim 17 | delete "comprisng:" and insert -- comprising: -- |
| Column 9, Line 49, Claim 17 | delete "sidewalk" and insert -- sidewalls -- |
| Column 9, Line 51, Claim 17 | delete "sidewalk" and insert -- sidewalls -- |
| Column 10, Line 66, Claim 21 | delete "sidewalks" and insert -- sidewalls -- |
| Column 12, Line 2, Claim 21 | delete "maiority" and insert -- majority -- |

Signed and Sealed this  
Twenty-sixth Day of May, 2020

Andrei Iancu  
*Director of the United States Patent and Trademark Office*